United States Patent [19]
Tesio

[11] Patent Number: 4,898,669
[45] Date of Patent: Feb. 6, 1990

[54] VASCULAR ACCESS DEVICE, IN PARTICULAR FOR PURIFICATION TREATMENTS OF THE BLOOD

[75] Inventor: Franco Tesio, Pordenone, Italy
[73] Assignee: Claber S.p.A., Italy
[21] Appl. No.: 206,105
[22] Filed: Jun. 13, 1988
[30] Foreign Application Priority Data
Jun. 16, 1987 [IT] Italy ................. 20908 A/87
[51] Int. Cl.$^4$ .................. B01D 13/00; A61M 5/00
[52] U.S. Cl. ..................... 210/232; 210/240; 210/321.72; 210/424; 137/625.47; 604/248
[58] Field of Search ............ 604/4, 5, 6, 175, 236, 604/905, 248; 210/232, 321.72, 321.73, 321.74, 321.75, 321.76, 321.77, 321.78, 321.79, 321.8, 321.81, 240, 418, 424, 239; 137/625.47

[56] References Cited
U.S. PATENT DOCUMENTS

| | | | |
|---|---|---|---|
| 3,626,938 | 12/1971 | Versaci | 137/625.47 |
| 4,015,601 | 4/1977 | Bokros et al. | 604/175 |
| 4,092,983 | 6/1978 | Slivenko | 604/175 |
| 4,108,173 | 8/1978 | Slivenko et al. | 604/175 |
| 4,108,174 | 8/1978 | Slivenko | 604/175 |
| 4,306,545 | 12/1981 | Ivan et al. | 604/175 |
| 4,654,033 | 3/1987 | Lapeyre et al. | 604/236 |

FOREIGN PATENT DOCUMENTS
2571260 4/1986 France .

*Primary Examiner*—W. Gary Jones
*Attorney, Agent, or Firm*—Steele, Gould & Fried

[57] ABSTRACT

A vascular access device includes a case having a first connection structured to couple with an end of a cut blood vessel such as an artery, a second connection structured to couple with an end of a cut blood vessel such as a vein, and access ports for removal means and admission means to be connected into the blood vessels. A valve is arranged in a rotating manner with two positions defining two independent passages. In a first position the valve establishes connection between the first connection and one of the access ports and between the second connection and the other of the access ports, respectively. The first position is apt for performance of a blood purification treatment. In a second position of the valve, one of the passages establishes mutual connection between the connections and the other of the passages establishes mutual connection between the access ports.

6 Claims, 4 Drawing Sheets

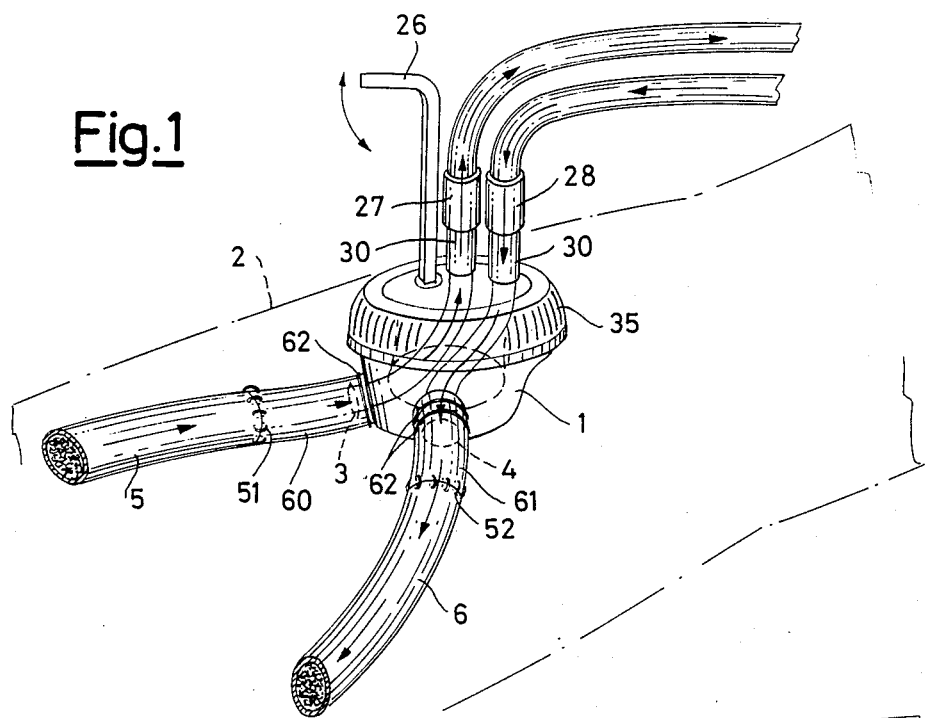
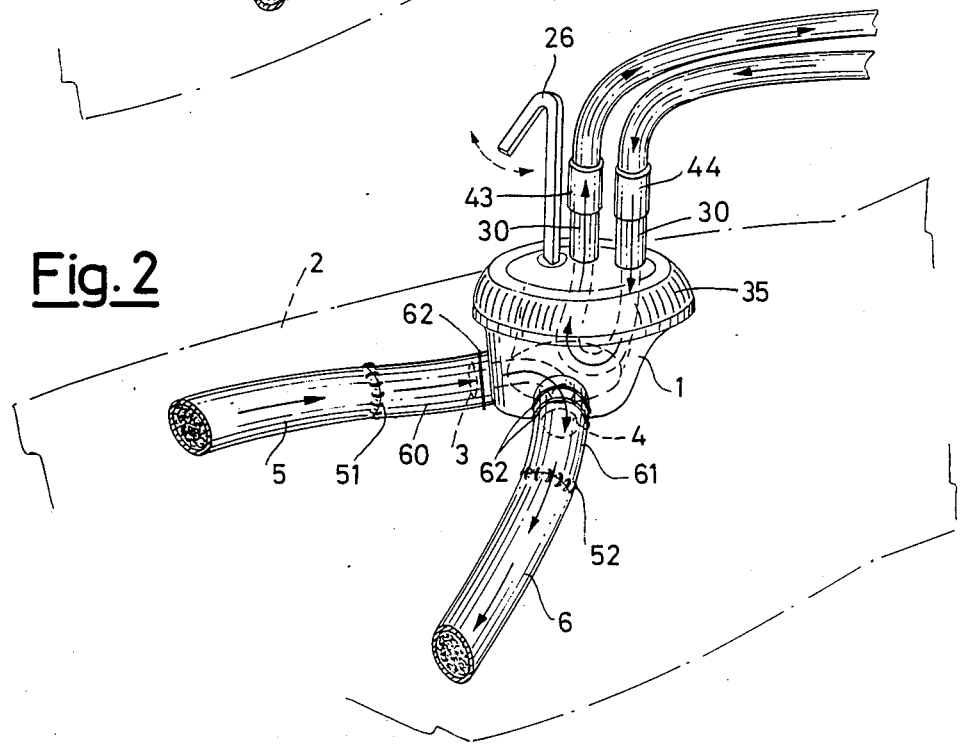

VASCULAR ACCESS DEVICE, IN PARTICULAR FOR PURIFICATION TREATMENTS OF THE BLOOD

BACKGROUND OF THE INVENTION

1. Field of the Invention

The present invention refers to a vascular access device, in particular for purification treatments of the blood.

2. Prior Art

There are many patients who must submit periodically and with a certain frequency to blood purification treatments such as dialysis. For these patients, in order to eliminate the repeated insertion of needles for taking the blood to be purified and the inlet of the purified blood, there have been developed recently the so-called 'vascular access' devices which are inserted permanently in the body of the patient and connected to his blood vessels.

Of this art a certain number of vascular access devices are known which comprise essentially a hollow body with apertures communicating with a duct integral therewith, which is grafted onto a blood vessel (artery or vein). Inside the hollow body there is housed a valve with passages which in one of its positions establishes communication between the blood vessel and external ducts connecting with means for removal and admission of the blood. By turning the valve said communication is interrupted. Examples of such devices are described in the patents FR 2571260, U.S. No. 4108174, U.S. No. 4015601, U.S. No. 4108173.

In some cases it was preferred to avoid removal and admission of the blood in the same zone and a vascular access device was achieved having two separate ducts inserted in different blood vessels (an artery and a vein) first connected through a fistule or bypass produced artificially. Said device is described in patents U.S. No. 4092983 and U.S. No. 4108174.

The drawback common to all the devices of the known art lies in the fact that not all the blood arriving in the vessel is routed to the purification equipment. A non-negligible part goes beyond the removal zone and mixes with the blood already purified. In addition, part of the returning blood can be recirculated by immediate intake back into the dialysis apparatus. As a result the efficiency of the purification treatment is reduced.

At the same time the formation of artificial fistules always calls for a surgical operation which it is not always possible to perform.

Another considerable drawback of said devices consists of the possible formation of coagulated blood and thrombi in the graft zone which must be removed quickly to avoid occlusion of the grafted duct.

Lastly, the need for periodic cleaning and maintenance of the device without removing said device from the body must be met.

SUMMARY OF THE INVENTION

In view of this state of the art an object of the present invention is to achieve a vascular access device for performing blood purification treatments which without requiring the formation of fistules upstream would allow removal of all the blood arriving within the blood vessel intercepted, thereby preventing mixing of the unpurified blood with the blood already purified.

Another object is to provide a vascular access device which would considerably reduce the possibility of the formation of thrombi.

Another object is to achieve a vascular access device which would make possible easy and fast cleaning and maintenance operations when necessary.

In accordance with the invention these objects are achieved by making a vascular access device in particular for purification treatment of the blood comprising a case designed to be grafted permanently in a living tissue and equipped with a pair of connections for blood vessels, a 2-position valve housed in said case and a pair of access openings for means of removal and admission of the blood. The connections are formed in such a manner as to couple with respective ends of cut blood vessels and said valve has two independent passages which in a first position of said valve establish respectively connection between a first connection and a first access opening and between the second connection and the second access opening while in a second position of the valve they establish respectively the connection between said first and said second connection and between said first and said second access opening.

In this manner with the valve in the aforesaid first position the blood can be taken from a first blood vessel such as an artery or from an upstream part of a single cut vessel (i.e., a vein or artery) and made to circulate to the dialysis apparatus to then be readmitted in a second blood vessel such as a vein or in a downstream part of said cut single vessel. With the valve in the second position at the same time one of the two passages of the valve allows the blood to pass freely from one vessel to the other or from one part to the other of the single cut vessel, leaving the possibility of performing cleaning of the passage in the period not involving blood circulation. The two passages can be reversed for cleaning of the other passage.

With such an arrangement of the connections in combination with a 2-duct valve there is obtained the removal of all the blood flow and readmission of the purified blood is effected without disturbing the normal venous flow.

The efficiency of the purification is increased, no arterial or venous fistules are required upstream, the formation of thrombi is made highly improbable, and easy, quick cleaning of the passages involved in the blood flow is possible for the removal of any thrombi.

BRIEF DESCRIPTION OF THE DRAWINGS

A possible practical embodiment of the present invention is illustrated as a nonlimiting example in the annexed drawings wherein:

FIG. 1 shows a perspective view of the vascular access device in accordance with the invention in operating position, FIG. 2 shows a perspective view of said device in the cleaning phase.

DETAILED DESCRIPTION OF THE PREFERRED EMBODIMENTS

Figure 3:
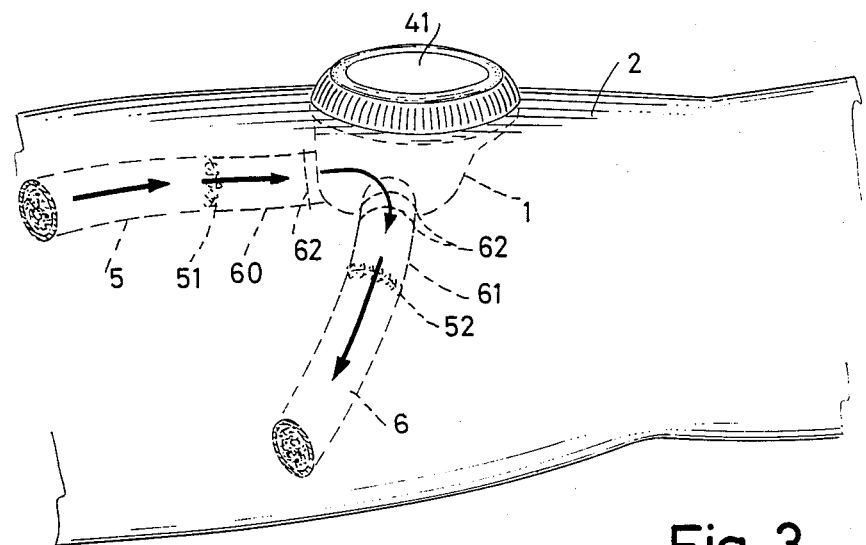
FIG. 3 shows a perspective view of said device in neutral position.

With reference to the annexed figures there is shown a vascular access device comprising a case 1 of rigid biocompatible plastic material (e.g. Teflon) designed to be grafted permanently in living tissue 2 (e.g. of an arm) and having two connections 3 and 4 for two ends 60 and 61 of artificial vessels sutured at 51 and 52 to blood vessels 5 and 6 respectively, such as an artery and a vein respectively or two separate parts of a single cut vessel (artery or vein). Said ends 60 and 61 are fixed to the connections 3 and 4 respectively by means of one or more lock rings 62. The outer surface of the case 1 is covered with a first layer 9 of rubbery dampening material (e.g. Silastic) on which is arranged a second layer of biologically compatible material 10 (e.g. Goretex) capable of being welded to the human tissue in which the device is grafted.

For better fixing of the device to the tissue in which it is grafted the layer of biologically compatible material 10 is fixed to the underlying muscle with suture stitches 63.

The connections 3 and 4 are in the form of sleeves with an interior passage 7 presenting a terminal section 8 flaring outward.

The case 1 has a cavity which describes a lower seat having a circular side wall 11 and a closed bottom 12 and an upper seat having side walls 13 and a partially open bottom 14. The case 1 comprises also unions 15 and 16 having the lower mouths 17 made in the side wall 11 of the lower seat and the upper flanged mouths 18 protruding from the bottom 14 of the upper seat (FIG. 5).

Within the lower seat of the case 1 is placed a valve 19 rotating around an axis perpendicular to the bottom 14 and within the upper seat 12 is placed a retaining element 20 having an opening 50 which surrounds part of said valve 19, said element 20 having in addition vertical passages (21 and 22) arranged in such a manner as to mate with the upper flared mouths of the unions 15 and 16 of the case 1.

Figure 4:
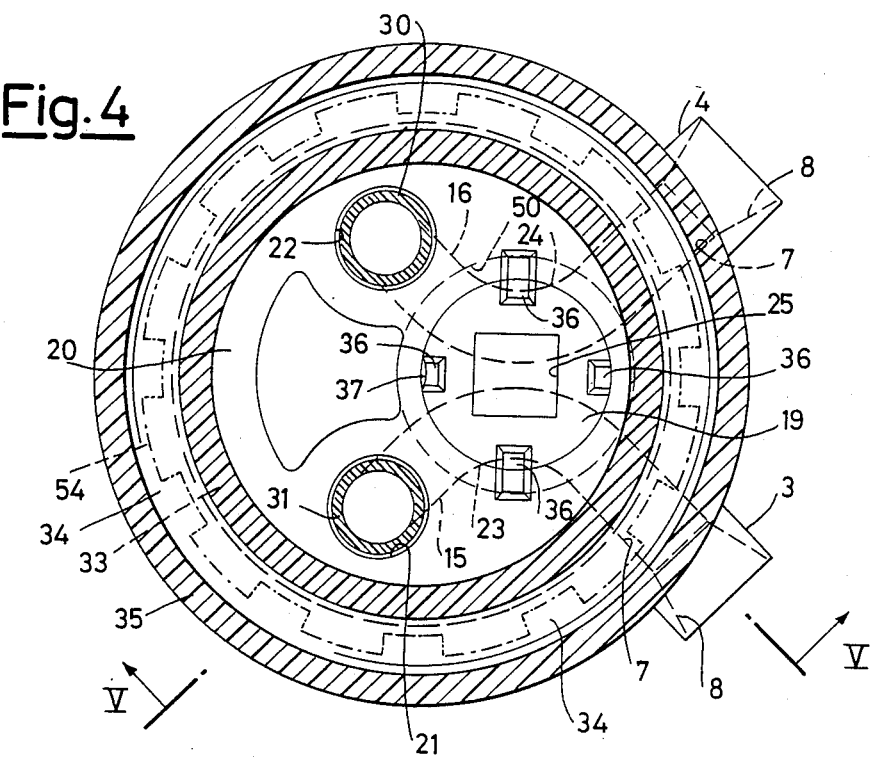
FIG. 4 shows a horizontal section of said device in the operating position of FIG. 1 along line IV—IV of FIG. 5.

The valve 19, as shown in FIG. 4, has two passages 23 and 24 with curved axis which form a system of communication between the inner passages 7 of said connections 3 and 4 of said unions 15 and 16 and a blind hole 25 for the introduction of a set screw wrench 26 (FIGS. 1 and 2) for operation of said valve.

Figure 5:
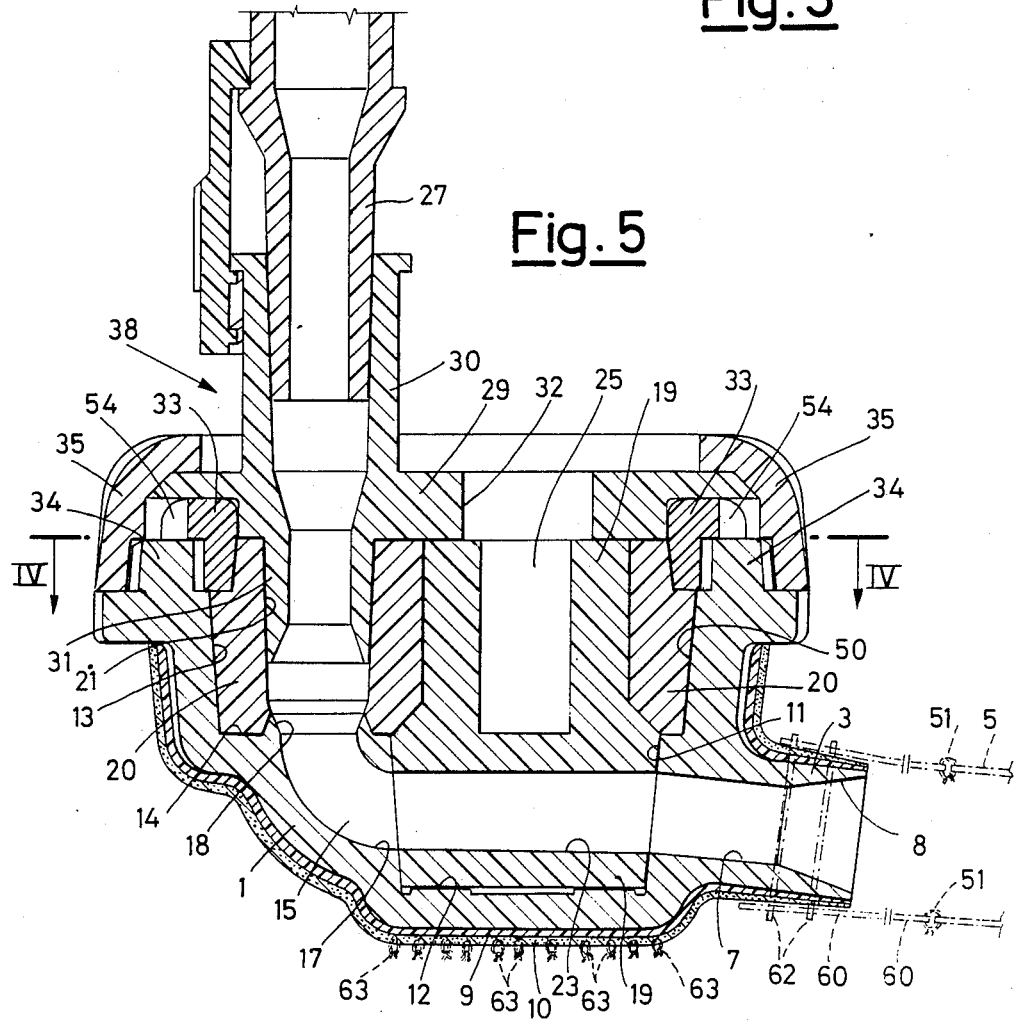
FIG. 5 shows a vertical section of said device along line V—V of FIG. 4.

In the position of FIGS. 4 and 5 the passage 23 connects the coupling 3 to the union 15 and then to the vertical passage 21 and the passage 24 connects the connection 4 to the union 16 and then to the vertical passage 22. In said passages 21 and 22 are introduced a blood removal catheter 27 and a blood admission catheter 28 respectively connected to the dialysis apparatus (not shown). For better application of said catheters 27 and 28 there is provided a plate 29 to be placed during use over said retaining element 20 and the valve 19 and having two projecting portions 38, each forming an upper sleeve 30 and a lower sleeve 31. The upper sleeves 30 are designed to receive removal catheters 27 and admission catheters 28 for the blood and the lower sleeves 31 are designed to penetrate in the vertical passages 21 and 22 of the retaining element 20 to constitute therewith access ports for said removal and admission catheters 27 and 28. The plate 29 also has an opening 32 corresponding with the blind hole 25.

The retaining element 20 is locked in the retaining position of the valve 19 by means of a ringnut 33 with a ridged or splined contour 54 screwed between the element 20 and the upper edge 34 of the case 1.

In addition, to retain the plate 29 in the operating position there is provided a shaped ring 35 screwed on the outer side of the edge 34 of the case 1.

Figure 6:
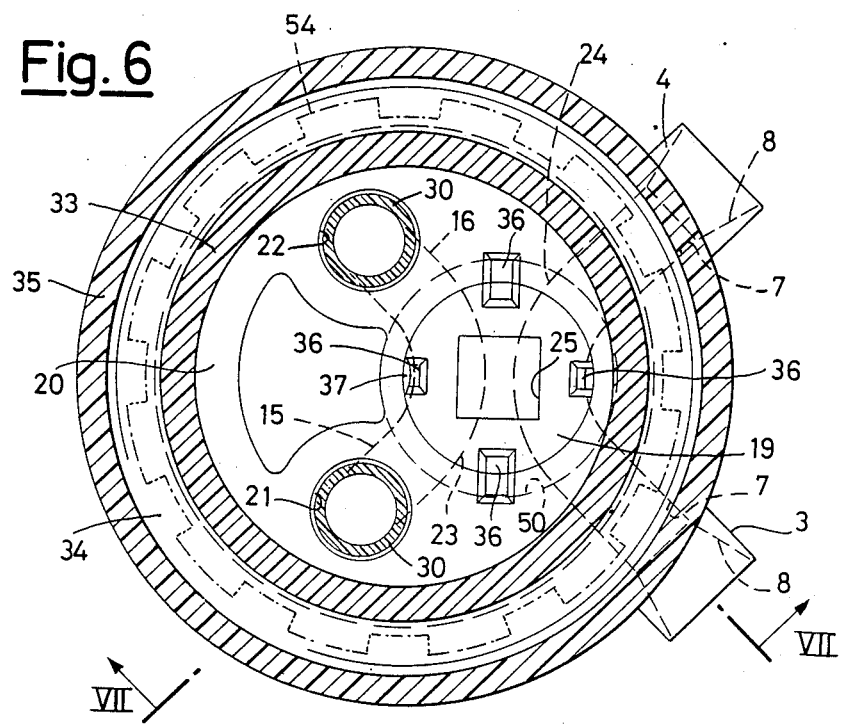
FIG. 6 shows a horizontal section of said device in the position of FIG. 2 along line VI—VI of FIG. 7.
Figure 7:
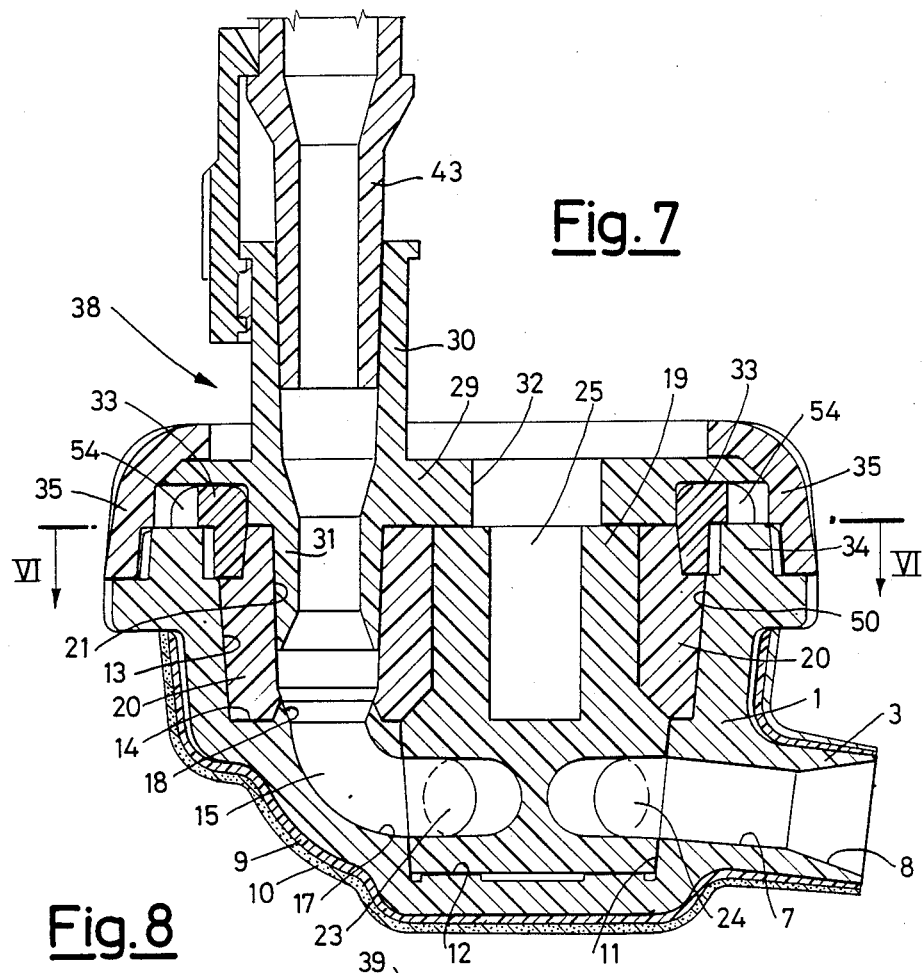
FIG. 7 shows a vertical section of said device along line VII—VII of FIG. 6.

Said plate 29 is applied to the retaining element 20 only when there are performed blood purification treatments (FIGS. 4 and 5) and subsequent cleaning of the device at the end of purification (FIG. 2), which is performed by arranging the valve 19 in the position shown in FIGS. 6 and 7. In other words, by rotating the valve 19 the passage 23 is brought to the connection position between the mouths 17 of the unions 15 and 16 simultaneously the passage 24 arranges itself for connection between the passages 7 of the connections 3 and 4, thus reestablishing normal blood circulation.

In order to accurately position the valve 19 there are provided in the body of the valve four notches 36 arranged at 90° angles from each other and which are selectively engaged by clips on a convex protrusion 37 provided on the surface of the opening 50 of the retaining element 20. Said clip system is useful for fixing the position of the valve during the blood purifying phase or the cleaning or neutral phase of the device, preventing any undesired rotation of the valve.

In the neutral position (FIG. 3) the shaped ring 35 and the plate 29 are removed and in their place are applied to the device a closing element 39 (FIG. 8), a layer of disinfecting material 40 and a cover 41 screwed, similarly to the shaped ring 35, on the edge 34 of the case 1. The closing element 39 has plugs 42 designed to penetrate in the vertical passages 21 and 22 of the retaining element 20.

The device described is designed to operate as follows.

Figure 8:
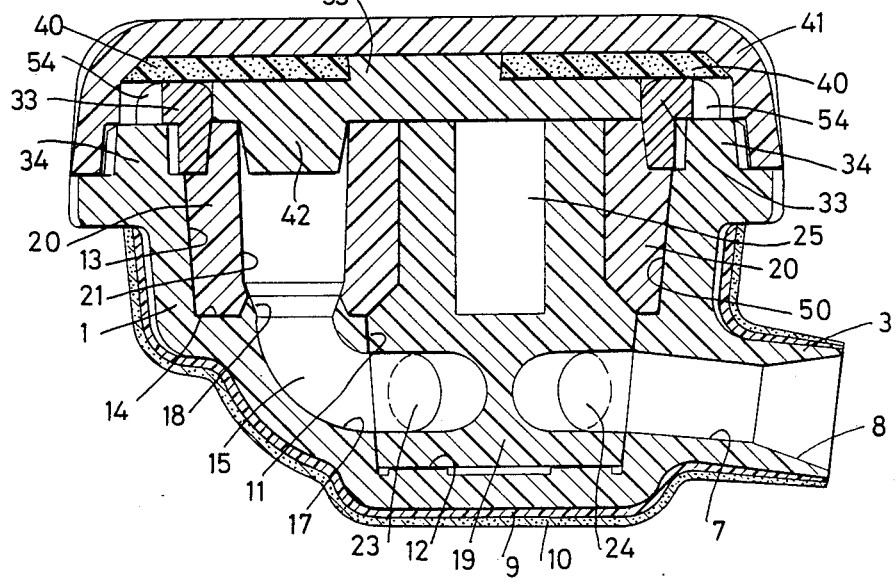
FIG. 8 shows a vertical section of said device in the neutral position of FIG. 3.

The patient to whom has been applied the device normally carries the device in a suitable part of the body, e.g. an arm as shown in FIG. 3. A connection (3) is preferably coupled in a precise manner to an end 60 of an artificial vessel sutured at 51 to a section of artery 5 appropriately cut and the other connection (4) is preferably coupled in the same manner by means of an end 61 to a section of vein 6 appropriately cut and reattached at 52. The arrangement of the parts of the device in neutral position is shown in FIG. 8, in other words one of the passages 23, 24 of the valve 19 constitutes the artery-vein connection while the other is inactive and constitutes a connection between the unions 15 and 16.

To proceed with the purification treatment the cover 41, the disinfecting material 40 and the closing element 39 are removed, and the plate 29 is applied causing the lower sleeves 31 to penetrate in the vertical passages 21 and 22 respectively. The plate is then locked by screwing on the case 1 the shaped ring 35. Finally, there are introduced in the sleeves 30 removal catheter 27 and admission catheter 28 for the blood (FIGS. 1 and 5). At this point are performed the connection between the artery 5 and the blood removal catheter 27 and between the vein 6 and the blood admission catheter 28 by rotating the valve 19 by 90° so that its passages 23 and 24 will be arranged as shown in FIGS. 4 and 5.

At the end of the purification phase the valve 19 is rotated again to interrupt communication of the blood vessels 5 and 6 with the passages 23 and 24 and hence with the respective unions 15 and 16 and the means 27 and 28 while the artery-vein connection is restored by, for example, the passage 24 as shown in FIGS. 6 and 7.

The passage 23 can now by cleaned, as it is in position connecting the unions 15 and 16, by introducing in the upper sleeves 30 of the plate appropriate cleaning tubes 43 and 44 which clean said duct 23, said unions 15 and 16 and said passages 21 and 22 (FIGS. 2, 6 and 7).

At the end of these operations the shaped ring 35 and the plate 29 are removed and the device is closed by applying the closing element 39, a new layer of disinfecting material 40 and the cover 41 (FIGS. 1 and 8).

It should be noted that the device described also allows easy maintenance of the operating parts of said device, in particular of the valve 19, with no need to remove the entire device and then reinsert it in the arm of the patient with further surgical operations.

This is achievable because once the cover 41 is unscrewed and the layer of disinfecting material and the closing element 39 have been removed it is also possible to unscrew the ringnut 33 and remove the retaining element 20 to finally gain access to the valve 19 and remove it from the case 1, which remains in position in the patient's arm. Naturally the connected vessels 5 and 6 will have to be blocked first, for example with an ordinary hemostatic loop.

I claim:

1. A vascular access device, comprising:
   a case designed to be grafted permanently in living tissue and having a pair of connections for blood vessels, the connections being structured to couple with respective ends of at least one cut blood vessel, the case having an outer surface covered with a first layer of damping material on which is arranged a second layer of biocompatible material weldable to the living tissue;
   a two-position valve removably housed in said case and a pair of access ports for removal means and admission means for blood, the valve being a rotary valve having two independent passages wherein, in a first rotational angular position of the valve the passages establish connection between a first of the connections and a first of the access ports and between a second of the connections and a second of the access ports, respectively, and in a second rotational angular position of the valve the passages establish connection between said first and second connections and between said first and second access ports, respectively, said access ports being formed in a retaining element for said valve and being connected to the passages by unions formed in the case, the retaining element being removably locked by a ringnut screwed onto the case; and,
   a plate having two portions, each of the portions having an upper sleeve and a lower sleeve, said upper sleeves being structured to receive said removal means and said admission means for the blood and said lower sleeves being structured to penetrate said access ports, the plate being lockable on the vascular access device by a shaped ring threadable onto the case.

2. The device of claim 1, further comprising a closing element, insertable and removable in said device, the closing element having stoppers designed to penetrate the access ports.

3. The device of claim 2, wherein said closing element is retained on the device by a cover screwed onto the case after placing between said element and said cover a layer of disinfecting material.

4. The device of claim 1, wherein said retaining element has an opening which surrounds said valve, said opening having on its surface a convex protrusion designed to snap, upon rotation of the valve, into notches provided on an edge of said valve at points designed to fix the device at an angular operating position and at an angular neutral position.

5. The device of claim 4, wherein rotation of the valve is accomplished with a set screw wrench inserted in a blind axial hole made in said valve.

6. The device of claim 1, wherein the access ports are connected to a blood dialyzer.

* * * * *